United States Patent [19]

Treybig et al.

[11] Patent Number: 4,725,373

[45] Date of Patent: Feb. 16, 1988

[54] NOVEL COMPOSITIONS PREPARED FROM ALKYL SUBSTITUTED NITROGEN-CONTAINING AROMATIC HETEROCYCLIC COMPOUNDS AND DICARBOXYLIC ACID MONOANHYDRIDES

[75] Inventors: Duane S. Treybig; James L. Potter, both of Lake Jackson, Tex.

[73] Assignee: The Dow Chemical Company, Midland, Mich.

[21] Appl. No.: 831,966

[22] Filed: Feb. 24, 1986

[51] Int. Cl.$^4$ .............................................. C23F 11/14
[52] U.S. Cl. .............................. 252/8.555; 252/392; 422/7; 422/16; 544/336; 546/339
[58] Field of Search ................. 252/8.555, 392, 8.553; 422/7, 12, 16; 544/336; 546/339

[56] References Cited

U.S. PATENT DOCUMENTS

| | | | |
|---|---|---|---|
| 2,490,744 | 12/1949 | Trigg et al. | 252/392 X |
| 2,643,977 | 6/1953 | Hughes | 252/8.55 |
| 3,077,454 | 2/1963 | Monroe et al. | 252/148 |
| 3,248,187 | 4/1966 | Bell, Jr. | 44/63 |
| 3,248,334 | 4/1966 | Monroe | 252/151 |
| 3,256,187 | 6/1966 | Davis | 252/34 |
| 3,278,427 | 10/1966 | Butcosk | 252/25 |
| 3,296,127 | 1/1967 | Butcosk et al. | 252/25 |
| 3,378,488 | 4/1968 | Nimerick | 252/8.55 |
| 3,658,707 | 4/1972 | Delafield et al. | 252/392 X |
| 3,762,873 | 10/1973 | Oude Alink | 252/392 X |
| 3,932,296 | 1/1976 | Byth | 252/148 |
| 4,089,650 | 5/1978 | Redmore | 252/392 X |
| 4,100,099 | 7/1978 | Asperger et al. | 252/189 |
| 4,102,804 | 7/1978 | Clouse et al. | 252/189 |
| 4,256,595 | 3/1981 | Sung et al. | 252/392 X |
| 4,315,087 | 2/1982 | Redmore et al. | 525/421 |
| 4,339,349 | 7/1982 | Martin et al. | 252/389 A |
| 4,362,860 | 12/1982 | Ratto et al. | 528/248 |
| 4,471,107 | 9/1984 | Peake | 528/248 |
| 4,515,708 | 5/1985 | Haslegrave et al. | 252/390 |

FOREIGN PATENT DOCUMENTS 42-14468 8/1967 Japan .

OTHER PUBLICATIONS

"Heterocyclic β-Diketoeamines: 1. 1,3-Indanediones Substituted at Position 2 with a Nitrogen Heterocycle" by J. Ploquin, L. Sparfel, G. LeBaut, R. Floc'h and Y. Letourneux, *J. Heterocyclic Chem.*, vol. 17, pp. 916–973 (1980).

"A Study of the Chemistry of Pyrophthalone and Related Compounds" by D. Manly, A. Richardson, Jr., A. Stock, C. Tilford and E. Amstutz, *J. Org. Chem.*, vol. 23, pp. 373–380 (1958).

"Reactivity of Methyl Groups During Condensation of 2,4-Lutidine and 2,4,6-Collidine with Phthalic Anhydride" by J. Ploquin, *C.R. Acad. Sc. Paris*, vol. 279, pp. 1149–1152 (1974).

*Chem. Abstr. 82:139901f* "Pyrophthalones, II, Synthesis and Pharmocodynamic Activity of Y-Pyrophthalones, Influence of Substituents on the Pyridine Ring" by J. Ploquin, L. Sparfel, G. LeBaut, R. Floc'h, L. Welin, J. Petit and N. Henry.

*Primary Examiner*—Herbert B. Guynn

[57] ABSTRACT

New compositions of matter are disclosed which are the products resulting from reacting an alkyl substituted aromatic heterocyclic nitrogen-containing compound such as 2,4,6-trimethylpyridine or 2,3,5,6-tetramethylpyrazine with a dicarboxylic acid monoanhydride such as 2-dodecen-1-yl succinic anhydride. These compositions are useful in preventing corrosion of metallic articles in corrosive environments. They are particularly useful in down hole oil and gas well applications.

18 Claims, No Drawings

NOVEL COMPOSITIONS PREPARED FROM ALKYL SUBSTITUTED NITROGEN-CONTAINING AROMATIC HETEROCYCLIC COMPOUNDS AND DICARBOXYLIC ACID MONOANHYDRIDES

BACKGROUND OF THE INVENTION

The present invention pertains to novel compositions prepared by reacting alkyl substituted nitrogen-containing aromatic heterocyclic compounds with dicarboxylic acid monoanhydrides.

During the drilling and servicing of oil and gas wells, the metal tools and equipment associated therewith are susceptible to corrosion. It is therefore highly desirable to have corrosion inhibitors for the protection of these metal tools and equipment. The present invention provides corrosion inhibitors for metals for use at both low and high temperatures. The deeper the wells, the higher the temperature; therefore there is a need for inhibitors suitable for protecting metals at both low and high temperatures.

SUMMARY OF THE INVENTION

One aspect of the present invention concerns new compositions of matter which comprises the reaction product of (A) at least one aromatic heterocyclic material having one or more rings, at least one nitrogen atom and at least one substituent group which has at least one reactive hydrogen atom attached to a carbon atom which is attached to the aromatic heterocyclic ring; and (B) at least one dicarboxylic acid monoanhydride; wherein said cyclic anhydride has a substituent saturated or unsaturated aliphatic hydrocarbon group having at least about 6 carbon atoms.

Another aspect of the present invention pertains to a corrosion inhibiting composition which comprises (A) from about 10 to about 99 percent by weight of a carrier liquid and (B) from about 1 to about 90 percent by weight of a corrosion inhibitor which is the product resulting from reacting (1) at least one aromatic heterocyclic material having one or more rings and at least one nitrogen atom and at least one substituent group which has at least one reactive hydrogen atom attached to a carbon atom which is attached to the heterocyclic ring and (2) at least one dicarboxylic acid monoanhydride; wherein components (1) and (2) are employed in quantities which provide a mole ratio of the aromatic heterocyclic material to dicarboxylic acid monoanhydride of from about 0.2:1 to about 5:1, preferably from about 0.8:1 to about 2:1, most preferably from about 1:1 to about 1.5:1.

Another aspect of the present invention pertains to a process for preventing or reducing the corrosion of a metallic article in contact with corrosive fluids, which process comprises contacting the surface of said metallic article with an effective amount of the aforementioned corrosion inhibitor compositions.

DETAILED DESCRIPTION OF THE INVENTION

The compositions of the present invention can be prepared by reacting at least one aromatic heterocyclic compound containing at least one nitrogen atom in the ring and containing at least one substituent group which has at least one reactive hydrogen atom attached to a carbon atom which is attached to the heterocyclic ring with at least one dicarboxylic acid monoanhydride. The reaction is conducted in the presence of a catalyst, accelerating agent or dehydrating agent and if desired the reaction can be conducted in the presence of a solvent. The components are employed in quantities which provide a mole ratio of the aromatic heterocyclic compound to dicarboxylic acid monoanhydride of from about 0.2:1 to about 5:1, preferably from about 0.8:1 to about 2:1, most preferably from about 1:1 to about 1.5:1. The reaction is conducted at a temperature of from about 50° C. to about 300° C., preferably from about 120° C. to about 220° C., most preferably from about 140° C. to about 180° C. The reaction can be prepared at pressures ranging from below atmospheric pressure up to the limits of the reaction vessel. It is preferred, however, to conduct the reaction at a pressure of from about 0.019 psig (0.13 kPa) to about 14.7 psig (101.36 kPa).

Suitable catalysts which can be employed include, for example, acids, Lewis acids, bases or salts. Particularly suitable acids include, for example, sulfuric, hydrochloric, acetic or p-toluene-sulfonic acid. Particularly suitable Lewis acids include boron trifluoride. Particularly suitable bases include, for example, hydroxides of alkali or alkaline earth metals or of quaternary ammonium. Particularly suitable salts include, for example, zinc chloride or aluminum chloride. The use of such catalysts is not indispensable but it reduces the time required for the reaction. The amount is e.g. of from about 0.1 to about 10 mole% with respect to the cycloaliphatic or aromatic carboxylic acid monoanhydride. If desirable, larger or lesser quantities can be employed.

The reaction can also be accelerated by certain substances such as methyl iodide, methyl sulfate, benzyl chloride, etc., capable of forming with the pyridinic and/or pyrazinic base quaternary ammonium derivatives, such substances being usable in catalytic amounts or higher proportions.

Dehydrating agents such as acetic anhydride, trifluoroacetic anhydride, propionic anhydride and the like can promote the reactions and its action can be sufficient to render superfluous the incorporation of a catalyst. The amount of anhydride used ranges from 1 to 10 moles per mole of monoanhydride, preferably 1.1 to 5. The preferred dehydrating medium is a mixture of glacial acetic acid and acetic anhydride. The acetic acid and acetic anhydride can be removed by distillation, solvent extraction, solvent fractionation or neutralization with a base. Examples of several solvent fractionation methods are described in U.S. Pat. Nos. 4,362,860 and 4,471,107 which are incorporated herein by reference.

Suitable solvents which can be employed include, for example, ketones, ethers, amides, acids, aromatic heterocycles containing no substituent groups which have at least one reactive hydrogen atom attached to a carbon atom which is attached to the aromatic heterocyclic ring, chlorinated solvents, hydrocarbons and the like. Particularly suitable solvents include, tetrahydrofuran, pyridine, xylene, glacial acetic acid, dimethylformamide, N,N-dimethylacetamide, N,N-diethylformamide, N,N-dimethylmethoxyacetamide, hexamethylphosphotriamide, N-methyl-pyrrolidinone, mixtures thereof and the like.

Suitable aromatic heterocyclic materials having one or more rings, at least one nitrogen atom and at least one substituent group which has at least one reactive hydrogen atom attached to a carbon atom which is attached to the aromatic heterocyclic ring which can be employed herein include, for example, pyrazines, pyridines, pyrazoles, imidazoles, pyridazines, pyrimidines, purines, pteridines, triazines, quinolines and quinoxalines. Particularly suitable such substituent groups include methyl, —CH(R)$_2$ or —CH$_2$R groups wherein each R is independently a hydrocarbyl group containing from 1 to about 20, preferably from 1 to about 10 carbon atoms.

The term hydrocarbyl as employed herein means any aliphatic, cycloaliphatic, aromatic, aryl substituted aliphatic or aliphatic substituted aromatic groups.

Particularly suitable as the heterocyclic material which can be employed herein include the pyrazines such as, for example, 2-methylpyrazine, 2,3-dimethylpyrazine, 2,5-dimethylpyrazine, 2,6-dimethylpyrazine, 2,3,5-trimethylpyrazine, 2,3,5,6-tetramethylpyrazine, 2-ethylpyrazine, 2-ethyl-3-methylpyrazine, 2-ethyl-5-methylpyrazine, 2-ethyl-6-methylpyrazine, 2-ethyl-3,5-dimethylpyrazine, 3-ethyl-2,5-dimethylpyrazine, 5-ethyl-2,3-dimethylpyrazine, 2-propylpyrazine, 2-methyl-3-propylpyrazine, 2-methyl-6-propylpyrazine, 2,5-dimethyl-3-propylpyrazine, 3,5-dimethyl-2-propylpyrazine, 2-(1-methylethyl)pyrazine, 2-methyl-3-(1-methylethyl)pyrazine, 2-methyl-5-(1-methylethyl)pyrazine, 6-methyl-2-(1-methylethyl)pyrazine, 2,3-diethylpyrazine, 2,3-diethyl-5-methylpyrazine, 3,5-diethyl-2-methylpyrazine, 2,6-diethyl-3,5-dimethylpyrazine, 2,5-diethyl-3,6-dimethylpyrazine, 2,5-bis(1-methylethyl)pyrazine, 2,5-dimethyl-3,6-bis(1-methylethyl)pyrazine, 2-butylpyrazine, 2-butyl-3-methylpyrazine, 2-butyl-6-methylpyrazine, 2-butyl-3,5-dimethylpyrazine, 3-butyl-2,5-dimethylpyrazine, 5-butyl-2,3-dimethylpyrazine, 2-butyl-3,5,6-trimethylpyrazine, 2,5-dibutyl-3,6-dimethylpyrazine, 2,5-dimethyl-3,6-bis(2-methylpropyl)pyrazine, 2,5-diethyl-3,6-bis(2-methylpropyl)pyrazine, 2-methyl-3-(2-methylpropyl)pyrazine, 2,3,5-trimethyl-6-(2-methylpropyl)pyrazine, 2-methyl-3-pentylpyrazine, 2-hexylpyrazine, 2-hexyl-3-methylpyrazine, 2,5-dimethyl-3,6-pyrazinediamine, 2,3,5-trimethyl-6-nitropyrazine, 2-chloro-3,5-dimethylpyrazine, mixtures thereof and the like.

Particularly suitable pyridines which can be employed herein include, for example, 2-methylpyridine, 4-methylpyridine, 2,3-dimethylpyridine, 2,4-dimethylpyridine, 2,5-dimethylpyridine, 2,6-dimethylpyridine, 2-ethylpyridine, 2,3,4-trimethylpyridine, 2,3,5-trimethylpyridine, 2,3,6-trimethylpyridine, 2,4,5-trimethylpyridine, 2,4,6-trimethylpyridine, 2-ethyl-3-methylpyridine, 2-ethyl-4-methylpyridine, 3-ethyl-2-methylpyridine, 3-ethyl-4-methylpyridine, 2-ethyl-6-methylpyridine, 5-ethyl-2-methylpyridine, 4-ethyl-2-methylpyridine, 2,4-diethylpyridine, 3,6-diethyl-2-methylpyridine, 2-ethyl-3,6-dimethylpyridine, 3-ethyl-2,6-dimethylpyridine, 4-ethyl-2,5-dimethylpyridine, 2-ethyl-4,6-dimethylpyridine, 2-methyl-4-propylpyridine, 2-methyl-4-(1-methylethyl)pyridine, 2-(1,1-dimethylethyl)-4-methylpyridine, 4-(1,1-dimethylethyl)-2-methylpyridine, 2,3-dimethyl-6-(1-methylethyl)pyridine, 3,6-dimethyl-2-(1-methylethyl)pyridine, 2,6-dimethyl-4-propylpyridine, 3,6-dimethyl-2-propylpyridine, 2-ethyl-3,4,6-trimethylpyridine, 3-ethyl-2,5,6-trimethylpyridine, 2-methyl-4-(1-methylpropyl)pyridine, 4-butyl-2-methylpyridine, 5-butyl-2-methylpyridine, 2,3,4,5-tetramethylpyridine, 2,3,4,6-tetramethylpyridine, 2,3,5,6-tetramethylpyridine, pentamethylpyridine, mixture thereof and the like.

Other suitable aromatic nitrogen containing heterocycles which can be employed herein include, pyrazoles, imidazoles, pyridazines, pyrimidines, purines, pteridines, triazines, quinolines and quinoxalines having one or more substituents having a reactive hydrogen atom attached to a carbon atom which is attached to a heterocyclic ring. Such substituent groups include methyl, —CH(R)$_2$ or —CH$_2$R wherein R is as above defined.

Suitable pyrazoles include 3-methylpyrazole, 3,5-dimethylpyrazole, 3,4,5-trimethylpyrazole, mixtures thereof and the like.

Suitable imidazoles which can be employed herein include, for example, 2-methylimidazole, 4-methylimidazole, 2,5-dimethylimidazole, 2,4-dimethylimidazole, 2,4,5-trimethylimidazole, 2-ethyl-4-methylimidazole, mixtures thereof and the like.

Suitable pyridazines include, for example, 3-methylpyridazine, 3,5-dimethylpyridazine, 3,4,5-trimethylpyridazine, 3,4-tripropylpyridazine, mixtures thereof and the like.

Suitable pyrimidines include, for example, 4-methylpyrimidine, 2,4-dimethylpyrimidine, 4,5-dimethylpyrimidine, 4,6-dimethylpyrimidine, 2,6-dimethyl-4-pyridinamine, 2,6-dimethyl-4-pyrimidinol, 2,4-dichloro-6-methylpyrimidine, 2,4,6-trimethylpyrimidine, 2,4-diethylpyrimidine, mixtures thereof and the like.

Suitable purines which can be employed herein include, for example, 6-methylpurine, 2,8-dimethylpurine, 2,8-dimethyl-6-purinamine, 2,6,8-trimethylpurine, mixtures thereof and the like.

Suitable pteridines include 6,7-dimethylpteridine, 2,6-dimethylpteridine, 2,4,7-trimethylpteridine, mixtures thereof and the like.

Suitable triazines which can be employed herein include 3,5-dimethyl-1,2,4-triazine, 3,6-dimethyl-1,2,4-triazine, 2,4-dimethyl-1,3,5-triazine, 2,4,6-trimethyl-1,3,5-triazine, mixtures thereof and the like.

Suitable quinolines include, for example, 2-methylquinoline, 4-methylquinoline, 2,4-dimethylquinoline, 2,6-dimethylquinoline, 2,7-dimethylquinoline, 8-ethyl-2-methylquinoline, 4-ethyl-2,3-dimethylquinoline, 8-ethyl-2,3-dimethylquinoline, 4-ethyl-2,3,8-trimethylquinoline, 4,8-diethyl-2,3-dimethylquinoline, 2,3-dimethyl-8-propylquinoline, 2,3,4-trimethyl-8-propylquinoline, 2,4-dimethyl-6-(1-methylpropyl)quinoline, mixtures thereof and the like.

Suitable quinoxalines include 2-methylquinoxaline, 2,5-dimethylquinoxaline, 2,3-dimethylquinoxaline, 2,6-dimethylquinoxaline, 2,3,6-trimethylquinoxaline, 2,3,6,8-tetramethylquinoxaline, mixtures thereof and the like.

The heterocyclic materials having one or more rings and at least one nitrogen atom and at least one substituent group which has at least one reactive hydrogen atom attached to a carbon atom which is attached to the aromatic heterocyclic ring can be mixed with each other. For example, 5-ethyl-2-methylpyridine can be mixed with 2-ethyl-3,5-dimethylpyrazine and used as the heterocyclic material in the present invention.

Suitable alkyl substituted nitrogen-containing aromatic heterocycles include the alkyl substituted pyridines, quinolines, pyrazines and quinoxalines listed in patent application Ser. No. 757,830, filed July 22, 1985 by Robert G. Martinez and Duane S. Treybig.

Suitable dicarboxylic acid monoanhydrides which can be employed herein include, for example, those represented by the formula:

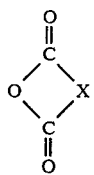

wherein X is a divalent radical which is substituted with a hydrocarbyl group or halogen, SH or OH substituted hydrocarbyl group having from about 1 to 40 carbon atoms. The term hydrocarbyl as employed herein means any aliphatic, cycloaliphatic, aromatic, aryl substituted aliphatic or aliphatic substituted aromatic groups. Examples of the X group are shown below:

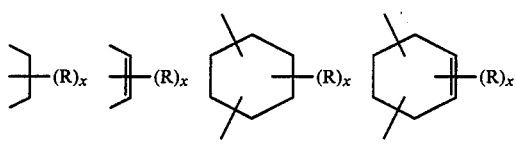

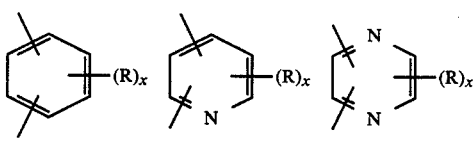

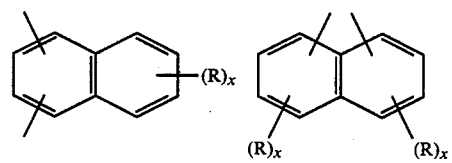

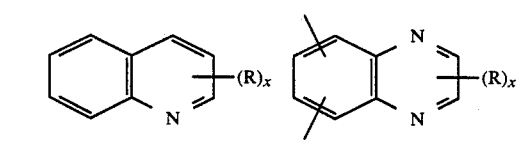

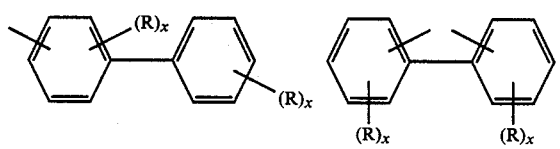

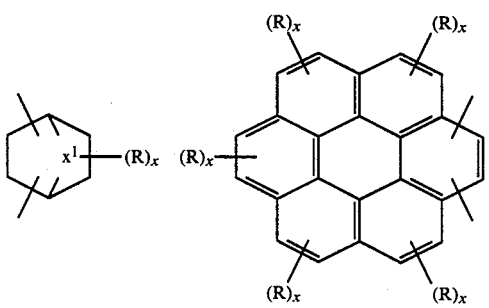

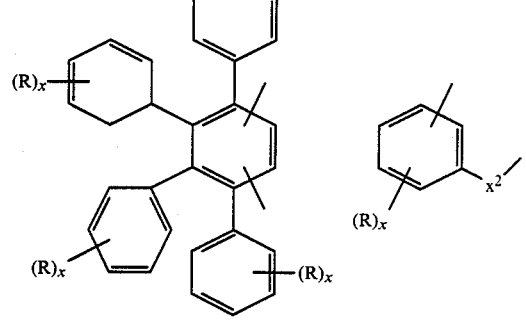

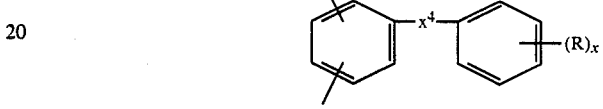

wherein each R is independently hydrogen or a saturated or unsaturated aliphatic group having from about 6 to about 40, preferably from about 10 to about 24, most preferably from about 12 to about 18 carbon atoms and which can be substituted with a halogen, SH or OH; $x^1$ is either $-CH_2-$, $-CH_2CH_2-$, $-O-$, $-NH-$, $-CCl_2-$ or $-S-$; $x^2$ is alkyl, or one of the following:

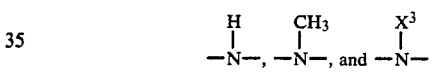

wherein $X^3$ is alkyl, aryl or aralkyl or such groups containing substituents such as, for example, halogen, nitro or amino and where $x^4$ is alkylene, oxygen, sulfur, oxyalkylene, polyoxyalkylene, or a group such as $-SO_2-$,

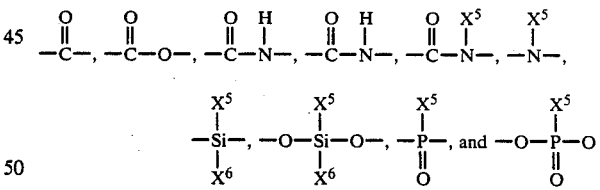

wherein $X^5$ and $X^6$ are alkyl, aryl or such groups containing substituents such as, for example, halogen, nitro or amino and x has a value from 1 to about 8.

The preferred monoanhydrides are those in which the carbon atoms of the pair of carbonyl groups are directly attached to ortho carbon atoms in the X group to provide a 5-member ring such as, for example,

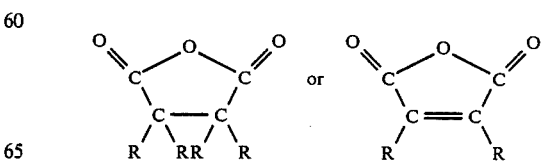

Suitable such dicarboxylic acid monoanhydrides include, for example, 1,3-isobenzofurandiones, hexahydro-1,3-isobenzofurandiones, 2,5-furandiones and dihydro-2,5-furandione. Suitable such 1,3-isobenzofurandiones which can be employed herein include those represented by the following formula

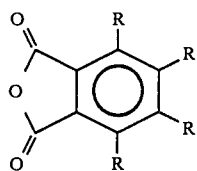

wherein R is either hydrogen, a saturated or unsaturated aliphatic hydrocarbon group having from about 6 to 40 carbon atoms, preferably from about 10 to about 24 carbon atoms, most preferably from about 12 to about 18 carbon atoms and which can be substituted with a halogen, —SH or —OH.

Particularly suitable 1,3-isobenzofurandiones include 5-dodecyl-1,3-isobenzofurandione, 4-hexadecyl-1,3-isobenzofurandione, 5-(2-hexadecenyl)-1,3-isobenzofurandione, 4-(2-hexadecenyl)-6-methyl-1,3-isobenzofurandione, mixtures thereof and the like.

Suitable hexahydro-1,3-isobenzofurandiones which can be employed herein include those represented by the following formula:

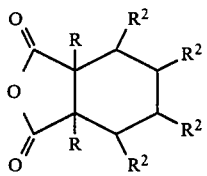

wherein R is either hydrogen, a saturated or unsaturated aliphatic hydrocarbon group having from about 6 to 40 carbon atoms, preferably from about 10 to about 24 carbon atoms, most preferably from about 12 to about 18 carbon atoms and which can be substituted with a halogen, —SH or —OH.

Particularly suitable hexahydro-1,3-isobenzofurandiones include 5-dodecylhexahydro-1,3-isobenzofurandione, 4-(2-hexadecenyl)hexahydro-1,3-isobenzofurandione, hexahydro-4-methyl-5-(2-octadecenyl)-1,3-isobenzofurandione, mixtures thereof and the like.

Suitable 2,5-furandiones which can be employed herein include those represented by the following formula:

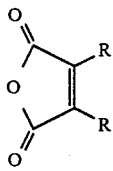

wherein R is either hydrogen, a saturated or unsaturated aliphatic hydrocarbon group having from about 6 to 40 carbon atoms, preferably from about 10 to about 24 carbon atoms, most preferably from about 12 to about 18 carbon atoms and which can be substituted with a halogen, —SH or —OH.

Particularly suitable 2,5-furandiones include 3-dodecyl-2,5-furandione, 3-octadecyl-2,5-furandione, 3-(2-octadecenyl)-2,5-furandione, 3-hexadecyl-4-methyl-2,5-furandione, mixtures thereof and the like.

Suitable dihydro-2,5-furandiones which can be employed herein include those represented by the following formula:

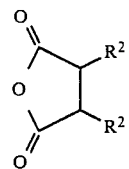

wherein R is either hydrogen, a saturated or unsaturated aliphatic hydrocarbon group having from about 6 to 40 carbon atoms, preferably from about 10 to about 24 carbon atoms, most preferably from about 12 to about 18 carbon atoms and which can be substituted with a halogen, —SH or —OH.

Particularly suitable dihydro-2,5-furandiones include 3-(2,4-diethyloctyl)dihydro-2,5-furandione, 3-dodecyldihydro-2,5-furandione, dihydro-3-(1-methyleneundecyl)-2,5-furandione, 3-cyclohexyldihydro-2,5-furandione, 3-(dodecylthio)dihydro-2,5-furandione, dihydro-3-(1-methyl-3-pentenyl)-2,5-furandione, dihydro-3-methyl-4-(3-pentenyl)-2,5-furandione, 3-(1-decenyl)-dihydro-2,5-furandione, 3-(2-decenyl)dihydro-2,5-furandione, 3-(1-dodecenyl)dihydro-2,5-furandione, 3-(2-dodecenyl)dihydro-2,5-furandione(2-dodecen-1-yl succinic anhydride), dihydro-3-(isododecenyl)2,5-furandione, dihydro-3-(tetrapropenyl)-2,5-furandione, dihydro-3-(pentadecenyl)-2,5-furandione, dihydro-3-(pentapropenyl)-2,5-furandione, 3-(2-hexadecenyl)dihydro-2,5-furandione, 3-(heptadecenyl)dihydro-2,5-furandione, dihydro-3-(isooctadecenyl)-2,5-furandione, dihydro-3-(2-octadecenyl)-2,5-furandione, dihydro-3-(1-octyl-2-decenyl)-2,5-furandione, 3-(1-ethenylhexadecyl)dihydro-2,5-furandione, 3-(hexapropenyl)dihydro-2,5-furandione, dihydro-3-(pentaisobutenyl)-2,5-furandione, 3-(eicosenyl)dihydro-2,5-furandione, 3-(docosenyl)dihydro-2,5-furandione, mixtures thereof and the like.

Thermal stability and film forming tenacity of a corrosion inhibitor is usually improved by some degree from crosslinking of the reactants. Tetracarboxylic acid dianhydrides can be mixed with dicarboxylic acid monoanhydrides to crosslink the reactants. Another necessary criteria for crosslinking the reactants is the presence of a nitrogen-containing aromatic heterocyclic compound having alkyl substituents with at least two reactive hydrogen atoms. Suitable tetracarboxylic acid dianhydrides which can be mixed with the above dicarboxylic acid monoanhydrides to crosslink the reactants include, pyromellitic dianhydride, benzene-1,2,3,4-tetracarboxylic dianhydride, pyridine-2,3,5,6-tetracarboxylic dianhydride, bis(2,3-dicarboxyphenyl)methane dianhydride, mixtures thereof and the like.

The compositions of the present invention can be employed as a corrosion inhibitor as are conventional corrosion inhibitors. Generally, the product can be employed in corrosion inhibitor formulations as are known in the art. For example, the product can be dispersed or dissolved in a suitable carrier liquid or solvent such as water, alcohols, aromatic and aliphatic hydrocarbons, and the like, or mixtures thereof. Other additives include demulsifiers, water wetting agents, surfactants, viscosifiers, commingled gases, defoamers, other corrosion inhibitors such as polymeric materials and salts, organic and inorganic acids, iron control agents, sequestering and/or chelating agents, phosphates, quaternaries, amine salts, and the like. For example, surface active agents are used to assure complete dispersion of active ingredients throughout the corrosion inhibitor composition and thus provide a better contact of the corrosion inhibitor with the surface of the metal compound which is being protected. The corrosion inhibitors of this invention form films on metal surfaces at least as readily as those known film forming corrosion inhibitors.

The corrosion inhibitor of this invention is employed in a functionally effective amount. That is, any quantity of corrosion inhibitor which will provide some degree of inhibition of corrosion is sufficient. Typical amounts of corrosion inhibitor which are employed in an oil and/or gas well treatment can range from about 5 to about 2,000 ppm for continuous treatment or about 1,000 to about 50,000 ppm for squeeze treatment, based on the weight of corrosive well fluids in contact with the metal compositions which are protected. Amounts of corrosion inhibitor in excess of 50,000 ppm can provide additional corrosion inhibition but at increased expense.

The corrosion inhibitors of this invention are highly stable to high temperatures and high pressures. Typically, corrosion inhibitors for oil and gas wells are employed in applications where temperatures range from about 100° F. (37.7° C.) to in excess of about 500° F. (260° C.), depending upon the composition of the product. The corrosion inhibitors of this invention are especially useful at temperatures ranging from 300° F. (148.8° C.) to about 450° F. (232.2° C.).

The corrosion inhibitors of this invention inhibit corrosion to metal compositions used in down hole applications, preferably in excess of 80 percent corrosion protection. The corrosion inhibitors advantageously inhibit corrosion of metal compositions at elevated temperatures exceeding 250° F. in oil and gas well applications. Useful applications include oil and/or gas well drilling, completion, workover, stimulation, transfer, processing and storage applications.

The following examples are illustrative of the present invention.

CORROSION TESTING, 175° F. (79.4° C.)

Corrosion inhibition of various samples was determined under conditions which simulate conditions that exist in oil and gas wells as follows. A brine solution containing 89.89 percent deionized water, 9.62 percent sodium chloride, 0.305 percent calcium chloride and a 0.186 percent hydrated magnesium chloride complex was prepared. This brine solution was purged with carbon dioxide until a pH of 3.8 was achieved. The solution was treated with sodium persulfate to remove oxygen. The desired corrosion inhibitor was added to the solution. About 720 milliliters (ml) of this brine solution and 80 ml of kerosene (90% brine/10% kerosene) treated with sodium persulfate were charged into a 32-ounce bottle. To this charge was added enough hydrated sodium sulfide to generate a suitable amount of hydrogen sulfide (i.e., about 300 ppm hydrogen sulfide based on total fluids).

Metal coupons (12"×¼"×1/16", 304.8 mm×6.35 mm×1.59 mm) of 1020 carbon steel were degreased with an inhibited methylchloroform, acidized with 16 percent hydrochloric acid, washed and dried. Each coupon weighed about 19 g. A metal coupon was placed in the bottle containing the brine, kerosene and ingredients as previously described. The bottle was capped and acetic acid was injected into the bottle through a septum. The bottle was placed on a vertically rotating wheel held at 175° F. (79.4° C.) and the sample was rotated at 26 rpm for 24 hours (86400 s). The coupons were removed from the bottle, cleaned, washed, dried, reweighed and the percent protection afforded them by the inhibitor was calculated by the following formula:

$$\text{percent protection} = 100 - \frac{\text{inhibitor coupon wt. loss}}{\text{blank coupon wt. loss}} \times 100$$

The weight loss was given to the nearest whole percent. The tests wherein no inhibitor is employed are for comparative purposes and are designated as blanks.

The corrosion rates were also determined in milliinches per year (mpy) by the following formula:

$$\text{mpy} = \frac{534 \text{ (Mg Weight Loss of Coupon)}}{d \times a \times t}$$

$d$ = density of 1020 carbon steel = 7.86 g/ml
$a$ = surface area (in.) of metal coupons
$t$ = test time in hours

CORROSION TESTING, 350° F. (177° C.)

The performance of 100 ppm of a corrosion inhibitor sample also was tested in a 350 ° F. (177° C.) wheel test containing 90 percent brine/8 percent heptane/2 percent kerosene at 2,000 psi pressure (25° C.) with 10 percent hydrogen sulfide, 10 percent carbon dioxide and 80 percent methane in a stainless steel pipe bomb. The sample was rotated at 26 rpm for 24 hours (86,400 s). Metal coupons (6"×¼"×1/16", 152.4 mm×6.35 mm×1.59 mm) of 1020 carbon steel were degreased with chlorothene, scrubbed, washed with acetone and dried before being placed in the pipe bomb. After the test, the coupons were removed from the pipe bomb, scrubbed, washed with acetone and dried. Percent protection was calculated using the same equations as in the above 175° F. corrosion test.

EXAMPLE 1

2,3,5,6-Tetramethylpyrazine (85.1 grams, 0.62 mole), 2-dodecen-1-yl succinic anhydride (99.5 grams, 0.37 mole) and glacial acetic acid (45.6 grams, 0.76 mole) were weighed into a 500 ml resin kettle equipped with an immersion thermometer, mechanical stirrer, condenser, addition funnel and nitrogen gas purge system. After the reactants were stirred and deoxygenated at 100° C. in a nitrogen atmosphere, acetic anhydride (76.5 grams, 0.75 mole) was added to the reactor. The reactants were heated between 94°–155° C. for 54 hours 4 minutes (194,640 s). After cooling to room temperature, the reactor contents were a black slightly viscous liquid that was soluble in acetone.

EXAMPLE 2

The black slightly viscous liquid from Example 1 was subjected to rotary evaporation under full vacuum at 100° C. Then the rotary evaporation bottoms were subjected to simple distillation with a vigreaux column at a bottoms temperature between 250°–280° C. and 33 mm mercury vacuum. The resulting distillation bottoms were a black viscous liquid. The black viscous liquid was found to contain 68.8% carbon, 10.9% hydrogen, 1.5% nitrogen and 18.8% oxygen by CHN analysis.

EXAMPLE 3

2,4,6-Trimethylpyridine (76.21 grams, 0.63 mole), 2-dodecen-1-yl succinic anhydride (99.60 grams, 0.37 mole) and glacial acetic acid (46.33 grams, 0.77 mole) were weighed into a reactor of the type described in Example 1. After the reactants were stirred and deoxygenated at room temperature in a nitrogen atmosphere for seven minutes (420 s), acetic anhydride (77.83 grams, 0.76 mole) was added to the reactor. The reactants were heated between 135°–147° C. for 52 hours 51 minutes (190,260 s). After cooling to room temperature, the reactor contents were a black liquid that was soluble in ethanol and xylene.

EXAMPLE 4

The black liquid from Example 3 was subjected to rotary evaporation under full vacuum at 100° C. for 70 minutes (4200 s). The resulting rotary evaporation bottoms were a black liquid that was soluble in xylene.

EXAMPLE 5

A mixture of alkyl substituted pyridines and alkyl substituted pyrazines (81.05 grams), 2-dodecen-1-yl succinic anhydride (100.08 grams, 0.38 mole) and glacial acetic acid (45.60 grams, 0.76 mole) were weighed into a reactor of the type described in Example 1. The mixture of alkyl substituted pyridines and alkyl substituted pyrazines consisted of 40.8 area percent 5-ethyl-2-methylpyridine, 42.0 area percent 3-ethyl-2,5-dimethylpyrazine and 3-ethyl-2,6-dimethylpyridine, and 17.2 area percent 2,3-dimethylpyridine, 2,3,6-trimethylpyridine, 3-ethyl-4-methylpyridine, 2,3,5-trimethylpyridine, 2-ethyl-4,6-dimethylpyridine, 3-methyl-5-propylpyridine, $C_5$-pyridine, $C_5$-pyrazine and $C_6$-pyrazine. The area percent of the constituents in the mixture was determined by using gas chromatography. After the reactants were stirred and deoxygenated at room temperature (25° C.) in a nitrogen atmosphere for 9 minutes (540 s), acetic anhydride (77.21 grams, 0.76 mole) was added to the reactor. The reactants were heated between 139°–145° C. for 50 hours 22 minutes (181,320 s). After cooling to room temperature, the reactor contents were a dark brown colored liquid. the dark brown colored liquid was dissolved in xylene for the corrosion inhibition tests.

EXAMPLE 6

The dark brown colored liquid from Example 5 was subjected to rotary evaporation under full vacuum at 100° C. for 40 minutes (2400 s). The rotary evaporation bottoms were a black liquid that was soluble in xylene. The black colored liquid was dissolved in xylene for the corrosion inhibition tests.

EXAMPLE 7

Polyisobutenyl succinic anhydride (96.24 grams, 0.095 mole, 1018 g/mole), the mixture of alkyl substituted pyridines and alkyl substituted pyrazines described in Example 5 (25.20 grams) and glacial acetic acid (25.62 grams, 0.427 mole) were weighed into a reactor of the type described in Example 1. After the reactants were stirred and deoxygenated at room temperature in a nitrogen atmosphere for 14 minutes (840 s), acetic anhydride was added to the reactor. The reactants were heated between 139°–142° C. for 48 hours 40 minutes (175,200 s). After cooling to room temperature, the reactor contents were a black viscous liquid. This liquid was rotary evaporated under full vacuum at 100° C. for 3 hours 40 minutes (13,200 s). The resulting rotary evaporation bottoms were dissolved in xylene for the corrosion inhibition tests.

EXAMPLE 8

2,3,5,6-Tetramethylpyrazine (86.42 grams, 0.63 mole) and 2-dodecen-1-yl succinic anhydride (96.78 grams, 0.36 mole) were weighed into a 4-neck 250 milliliter round bottom flask equipped with an immersion thermometer, condenser, addition funnel, mechanical stirrer and nitrogen gas purge system. After the reactants were stirred at room temperature in a nitrogen atmosphere for 7 minutes (420 s), concentrated sulfuric acid (1.13 grams, 0.012 mole) was added to the reactor. The reactants were heated between 160°–189° C. for 31 hours 8 minutes (112,080 s). 1-Pentanol (133 grams) and additional concentrated sulfuric acid (3.22 grams, 0.033 mole) was added to the reactor contents. The reactants were heated between 139°–175° C. for an additional 18 hours 54 minutes (68,040 s). After cooling to room temperature, the reactor contents were a dark brown liquid that was soluble in xylene and ethanol.

EXAMPLE 9

2,4,6-Trimethylpyridine (75.02 grams, 0.62 mole) and 2-dodecen-1-yl succinic anhydride (100.47 grams, 0.38 mole) were weighed into a reactor of the type described in Example 8. Concentrated sulfuric acid (1.2 grams, 0.012 mole) was added to the stirring reactor contents. Then the reactants were heated between 158°–178° C. for 48 hours 50 minutes (175,800 s). The reactor contents were sampled. The sample was a dark brown liquid.

EXAMPLE 10

The reactor in Example 9 was fitted with a still head and its contents were subjected to distillation between 155°–215° C. and 157–202 mm mercury vacuum for 37 minutes (2220 s). The resulting product was a dark brown viscous liquid that was soluble in ethanol and xylene. The dark brown viscous liquid was found to contain 76.3% carbon, 11.7% hydrogen, 0.6% nitrogen and 11.4% oxygen by CHN analysis. The infrared Fourier Transform spectrum of the liquid supported the presence of unreacted 2-dodecen-1-yl succinic anhydride, carboxylic acid and a cyclic diketone which can be represented by the formula,

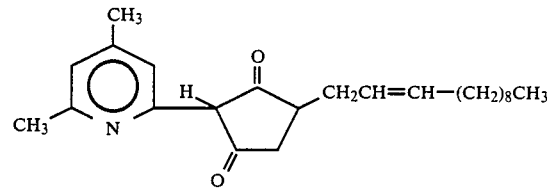

The presence of carboxylic acid was supported by a very broad, intense O—H stretching absorption between 3300-2500 $cm^{-1}$ and a band at 1709 $cm^{-1}$ due to the asymmetrical carbonyl (C=O) stretching vibration. The presence of the cyclic ketone was supported by absorption bands at 1616 $cm^{-1}$, 1636 $cm^{-1}$, 1656 $cm^{-1}$ and 1676 $cm^{-1}$ due to the carbonyl stretching vibration and bands at 1516 $cm^{-1}$ and 1563 $cm^{-1}$ which were assigned to —C═C— and —C═N— stretch. J. Ploquin et al in *J. Heterocyclic Chem.*, 1980, Vol. 17, pp. 17–18 reported similar wave numbers for the carbonyl absorption bands of 2-(5,6-dimethyl-2-pyridyl)-1,3-indanedione and 2-(5,6-dimethyl-2-pyridyl)-1,3-indanedione. The dark brown liquid was dissolved in a mixture of ethanol and xylene for the corrosion inhibition tests.

EXAMPLE 11

2,4,6-Trimethylpyridine (78.60 grams, 0.65 mole) and 2-dodecen-1-yl succinic anhydride (99.86 grams, 0.38 mole) were weighed into a reactor of the type described in Example 8. Zinc chloride (1.34 grams, 0.0098 mole) was added to the stirring reactor contents. Then the reactants were then heated between 153°–168° C. for 47 hours 20 minutes (170,400 s). The dark reddish brown colored liquid was sampled.

EXAMPLE 12

The reactor in Example 11 was fitted with a still head and its contents were subjected to distillation between 166°–224° C. and 160–217 mm mercury vacuum for 39 minutes (2340 s). The resulting product was a viscous reddish brown colored liquid that was soluble in xylene and ethanol. The reddish brown liquid was found to contain 73.8% carbon, 11.3% hydrogen, 0.7% nitrogen and 14.2% oxygen by CHN analysis. The infrared Fourier Transform spectrum of the reddish brown liquid differed from the spectrum of the product of Example 10 by the presence of more intense absorption bands at 1065 cm$^{-1}$ and 1709 cm$^{-1}$. The viscous reddish brown liquid was dissolved in a mixture of ethanol and xylene for the corrosion inhibition tests.

EXAMPLE 13

2,4,6-Trimethylpyridine (181.32 grams, 1.5 moles) and dodecenyl succinic anhydride (100.03 grams, 0.38 mole) were weighed into a reactor of the type described in Example 8. Dodecenyl succinic anhydride is the reaction product of tetrapropylene with maleic anhydride [dihydro-3-(tetrapropenyl)-2,5-furandione] and is commercially availble from Dixie Chemical Company. Concentrated sulfuric acid (1.16 grams, 0.012 mole) was added to the stirring reactor contents at 28° C. Then the reactants were heated between 163°–179° C. for a period of 2020 minutes (121,200 s). The reaction temperature was increased from 163° C. to 197° C. over a period of 337 minutes (20,220 s) as the Barrett trap contents were removed. The reactor was fitted with a still head and its contents were subjected to distillation between 199°–225° C. and 38–43 mm mercury vacuum for 38 minutes (2280 s). The reactor contents were cooled to room temperature giving a black viscous liquid. The black viscous liquid was dissolved in xylene for the corrosion inhibition tests.

EXAMPLE 14

2,4,6-Trimethylpyridine (143.49 grams, 1.18 moles) and a mixture (100.78 grams, 0.30 mole) of 50 wt.% hexadecenyl succinic anhydride [3-(hexadecenyl)dihydro-2,5-furandione] with 50 wt.% octadecenyl succinic anhydride [dihydro-3-(octadecenyl)-2,5-furandione] were weighed into a reactor of the type described in Example 8. The mixture of hexadecenyl succinic anhydride with octadecenyl succinic anhydride is commercially available from Dixie Chemical Company. Zinc chloride (1.07 grams, 0.007 mole) was added to the stirring reactor contents at 114° C. Then the reactants were heated between 162°–171° C. for a period of 1951 minutes (117,060 s). As the Barrett contents were removed, the reaction temperature was increased from 171° C. to 218° C. over a period of 419 minutes (25,140 s). The reactor was fitted with a still head and its content were subjected to distillation between 202°–226° C. and 182–243 mm mercury vacuum for 105 minutes (6300 s). The reactor contents were cooled to room temperature giving a dark brown liquid. The dark brown liquid was dissolved in xylene for the corrosion inhibition tests.

The corrosion protection of Examples 1 through 14 was determined by the 80° C. (175° F.) batch wheel test procedure. The results are given in Table I.

TABLE I

| Test No. | Inhibitor Type | Concentration | Weight Loss (g) | MPY[1] | Percent Protection |
|---|---|---|---|---|---|
| A-1[3] | None | 0 ppm | 0.1919 | 75.6 | 0 |
| A-2 | Ex. 1 | 100 | 0.0163 | 6.4 | 92 |
| B-1[3] | None | 0 | 0.1868 | 71.7 | 0 |
| B-2 | Ex. 2 | 100 | 0.0157 | 6.1 | 92 |
| C-1[3] | None | 0 | 0.1912 | 73.1 | 0 |
| C-2 | Ex. 3 | 100 | 0.0164 | 6.3 | 91 |
| C-3 | Ex. 5 | 100 | 0.0217 | 8.5 | 89 |
| D-1[3] | None | 0 | 0.1886 | 73.3 | 0 |
| D-2 | Ex. 4 | 100 | 0.0081 | 3.1 | 96 |
| D-3 | Ex. 6 | 100 | 0.0186 | 7.2 | 90 |
| D-4 | Ex. 7 | 100 | 0.0804 | 30.7 | 57 |
| E-1[3] | None | 0 | 0.1721 | 65.6 | 0 |
| E-2 | 2-Dodecen-1-yl succinic anhydride | 100 | 0.1872 | 71.6 | 0 |
| E-3 | Ex. 8 | 100 | 0.0097 | 3.7 | 94 |
| F-1[3] | None | 0 | 0.2097 | 78.7 | 0 |
| F-2 | 2,3,5,6-Tetramethylpyrazine in methanol | 100 | 0.1010 | 37.9 | 52 |
| G-1[3] | None | 0 | 0.1747 | 67.0 | 0 |
| G-2 | Ex. 9 | 100 | 0.0038 | 1.4 | 98 |
| G-3 | Ex. 10 | 100 | 0.0060 | 2.3 | 97 |
| G-4 | Ex. 11 | 100 | 0.0074 | 2.9 | 96 |
| G-5 | Ex. 12 | 100 | 0.0032 | 1.2 | 98 |
| H-1[3] | None | 0 | 0.1975 | 75.6 | 0 |
| H-2 | Ex. 13 | 100 | 0.0046 | 1.7 | 98 |
| H-3 | Ex. 14 | 100 | 0.0151 | 5.7 | 92 |
| I-1[3] | None | 0 | 0.3328 | 131.0 | 0 |
| I-2 | Corban[2] A-163 | 100 | 0.0658 | 26.0 | 80.2 |

[1]MPY is mils per year
[2]Corban A-163 is a commercial corrosion inhibitor available from Dowell-Schlumberger
[3]Not an example of this invention The data in Table I demonstrates that 100 ppm of the inhibitors of this invention exhibit good corrosion protection under simulated down hole tests at 80° C. In most cases, corrosion protection is significantly better than that exhibited by 2-dodecen-1-yl succinic anhydride, 2,3,5,6-tetramethylpyrazine and Corban A-163. Therefore, the corrosion inhibitors of this invention are suitable for the protection of metal alloys against corrosion due to corrosive fluids produced in oil and gas well formations and harmful to said metal alloys at or below 80° C. In addition, the corrosion inhibitors of this invention are suitable for the corrosion protection of pipelines, storage tanks, pumps, etc., that exist for the purpose of separating, recovering, oil and/or gas from the produced fluids.

The corrosion protection of Examples 1, 2, 3 and 6 was also determined by the 177° C. (350° F.) batch wheel test procedure. The results are given in Table II.

TABLE II

| Test No. | Inhibitor Type | Concentration | Weight Loss (g) | Percent Protection |
|---|---|---|---|---|
| A-1 | None | 0 | 0.1358 | 0 |
| A-2 | Example 1 | 100 | 0.0344 | 75 |
| A-3 | Example 2 | 100 | 0.0335 | 76 |
| B-1* | None | 0 | 0.0997 | 0 |
| B-2 | Example 3 | 100 | 0.0398 | 60 |
| B-3 | Example 6 | 100 | 0.0346 | 65 |

*Not an example of the present invention

The above data shows that the inhibitors of this invention advantageously provide good corrosion protection at 177° C. (350° F.) demonstrating the value of these inhibitors for high temperature and high pressure oil and gas well down hole environments.

We claim:

1. A corrosion inhibitor composition comprising (A) from about 10 to about 99 percent by weight of a carrier liquid and (B) from about 1 to about 90 percent by weight of a corrosion inhibitor which is the product resulting from reacting at a temperature of from about 50° C. to about 300° C. (1) at least one pyridine compound or pyrazine compound or a combination of such compounds, said compounds having at least one substituent group which has at least one reactive hydrogen atom attached to a carbon atom which is attached to the pyridine or pyrazine ring; and (2) at least one dicarboxylic acid monoanhydride represented by the following formulas I, II, III or IV

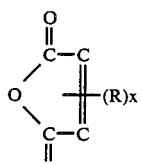

I.

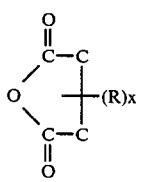

II.

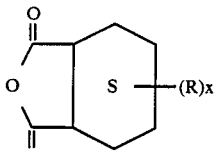

III.

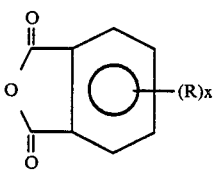

IV.

wherein each R is independently hydrogen or a saturated or unsaturated hydrocarbon group having from 6 to about 40 carbon atoms which can be substituted with a halogen, —SH or —OH, with the proviso that at least one R group is other than hydrogen and x has a value from 1 to about 8; and wherein components (1) and (2) are employed in quantities which provide a mole ratio of the aromatic heterocyclic compound to dicarboxylic acid monoanhydride of from about 0.2:1 to about 5:1.

2. A corrosion inhibitor composition of claim 1 wherein
   (i) components (B-1) and (B-2) are employed in quantities which provide a mole ratio of the pyridine or pyrazine compound to dicarboxylic acid monoanhydride of from about 0.8:1 to about 2:1; and
   (ii) in component (B-2) the substituent group has from 10 to about 24 carbon atoms.

3. A corrosion inhibitor composition of claim 2 wherein
   (i) components (B-1) and (B-2) are employed in quantities which provide a mole ratio of the pyridine or pyrazine compound to dicarboxylic acid monoanhydride of from about 1:1 to about 1.5:1; and
   (ii) in component (B-2) the substituent group has from 12 to about 18 carbon atoms.

4. A composition of claim 1 wherein component (B-2) is represented by formulas I or II or a combination thereof.

5. A composition of claim 4 wherein
   (i) component (B-1) is 2,4,6-trimethylpyridine, 5-ethyl-2-methylpyridine, 3-ethyl-2,6-dimethylpyridine, 3-ethyl-2,5-dimethylpyrazine, 2,3,5,6-tetramethylpyrazine, or a combination thereof; and
   (ii) component (B-2) is 3-(2-dodecenyl)dihydro-2,5-furandione, 3-(hexadecenyl)dihydro-2,5-furandione, dihydro-3-(octadecenyl)-2,5-furandione, dihydro-3-(tetrapropenyl)-2,5-furandione, or a combination thereof.

6. A composition of claim 2 wherein component (B-2) is represented by formulas I or II or a combination thereof.

7. A composition of claim 6 wherein
   (i) component (B-1) is 2,4,6-trimethylpyridine, 5-ethyl-2-methylpyridine, 3-ethyl-2,6-dimethylpyridine, 3-ethyl-2,5-dimethylpyrazine, 2,3,5,6-tetramethylpyrazine, or a combination thereof; and
   (ii) component (B-2) is 3-(2-dodecenyl)dihydro-2,5-furandione, 3-(hexadecenyl)dihydro-2,5-furandione, dihydro-3-(octadecenyl)-2,5-furandione, dihydro-3-(tetrapropenyl)-2,5-furandione, or a combination thereof.

8. A composition of claim 3 wherein component (B-2) is represented by formulas I or II or a combination thereof.

9. A composition of claim 8 wherein
   (i) component (B-1) is 2,4,6-trimethylpyridine, 5-ethyl-2-methylpyridine, 3-ethyl-2,6-dimethylpyridine, 3-ethyl-2,5-dimethylpyrazine, 2,3,5,6-tetramethylpyrazine, or a combination thereof; and
   (ii) component (B-2) is 3-(2-dodecenyl)dihydro-2,5-furandione, 3-(hexadecenyl)dihydro-2,5-furandione, dihydro-3-(octadecenyl)-2,5-furandione, dihydro-3-(tetrapropenyl)-2,5-furandione, or a combination thereof.

10. A process for preventing or reducing the corrosion of a metallic article in contact with a corrosive fluid, which process comprises contacting said metallic article with an effective amount of a corrosion inhibitor composition of claim 1 so as to prevent or reduce the corrosion of the metallic article.

11. A process for preventing or reducing the corrosion of a metallic article in contact with a corrosive fluid, which process comprises contacting said metallic article with an effective amount of a corrosion inhibitor composition of claim 2 so as to prevent or reduce the corrosion of the metallic article.

12. A process for preventing or reducing the corrosion of a metallic article in contact with a corrosive fluid, which process comprises contacting said metallic article with an effective amount of a corrosion inhibitor composition of claim 3 so as to prevent or reduce the corrosion of the metallic article.

13. A process for preventing or reducing the corrosion of a metallic article in contact with a corrosive fluid, which process comprises contacting said metallic article with an effective amount of a corrosion inhibitor composition of claim 4 so as to prevent or reduce the corrosion of the metallic article.

14. A process for preventing or reducing the corrosion of a metallic article in contact with a corrosive fluid, which process comprises contacting said metallic article with an effective amount of a corrosion inhibitor composition of claim 5 so as to prevent or reduce the corrosion of the metallic article.

15. A process for preventing or reducing the corrosion of a metallic article in contact with a corrosive fluid, which process comprises contacting said metallic article with an effective amount of a corrosion inhibitor composition of claim 6 so as to prevent or reduce the corrosion of the metallic article.

16. A process for preventing or reducing the corrosion of a metallic article in contact with a corrosive fluid, which process comprises contacting said metallic article with an effective amount of a corrosion inhibitor composition of claim 7 so as to prevent or reduce the corrosion of the metallic article.

17. A process for preventing or reducing the corrosion of a metallic article in contact with a corrosive fluid, which process comprises contacting said metallic article with an effective amount of a corrosion inhibitor composition of claim 8 so as to prevent or reduce the corrosion of the metallic article.

18. A process for preventing or reducing the corrosion of a metallic article in contact with a corrosive fluid, which process comprises contacting said metallic article with an effective amount of a corrosion inhibitor composition of claim 9 so as to prevent or reduce the corrosion of the metallic article.

* * * * *